(12) United States Patent
Park et al.

(10) Patent No.: US 12,027,310 B2
(45) Date of Patent: Jul. 2, 2024

(54) DUAL HYBRID ELECTROMAGNET MODULE FOR CONTROLLING MICROROBOT

(71) Applicant: KOREA INSTITUTE OF MEDICAL MICROROBOTICS, Gwangju (KR)

(72) Inventors: Jong Oh Park, Gyeonggi-do (KR); Ja Young Kim, Daejeon (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 571 days.

(21) Appl. No.: 17/318,054

(22) Filed: May 12, 2021

(65) Prior Publication Data

US 2022/0246339 A1 Aug. 4, 2022

(30) Foreign Application Priority Data

Jan. 29, 2021 (KR) .......................... 10-2021-0013298

(51) Int. Cl.
*H01F 7/08* (2006.01)
*A61B 34/00* (2016.01)
(Continued)

(52) U.S. Cl.
CPC ............. *H01F 7/081* (2013.01); *A61B 34/30* (2016.02); *A61B 34/73* (2016.02); *B25J 7/00* (2013.01); *B25J 9/12* (2013.01); *B25J 19/0054* (2013.01); *G05B 19/4155* (2013.01); *H01F 7/0205* (2013.01); *H01F 7/064* (2013.01);
(Continued)

(58) Field of Classification Search
CPC ........ H01F 7/081; H01F 7/0205; H01F 7/064; H01F 27/24; H01F 27/2823; H01F 7/0273; H01F 7/20; A61B 34/30; A61B 34/73; A61B 2034/731; A61B 34/72; A61B 2017/00345; B25J 7/00; B25J 9/12; B25J 19/0054; G05B 19/4155; G05B 2219/40269; G05B 2219/45073
See application file for complete search history.

(56) References Cited

U.S. PATENT DOCUMENTS 10,874,467 B2 * 12/2020 Azizian ................ A61B 34/37
2010/0204713 A1 * 8/2010 Ruiz Morales .......... B25J 9/041
606/130

(Continued)

FOREIGN PATENT DOCUMENTS

JP 2001307919 A * 11/2001
KR 20010015464 A * 2/2001
(Continued)

*Primary Examiner* — Mohamad A Musleh
(74) *Attorney, Agent, or Firm* — Harness, Dickey & Pierce, P.L.C.

(57) ABSTRACT

The present disclosure relates to a dual hybrid electromagnet module for controlling a microrobot. More specifically, the present disclosure relates to an electromagnetic field system in which a dual hybrid electromagnet module including a permanent magnet and an electromagnet is used for controlling a microrobot so that it is possible to reduce the number of used electromagnets so as to reduce power consumption and the amount of heat generated from the electromagnet module. The electromagnetic field system is capable of being used for various medical procedures and surgeries using a microrobot.

16 Claims, 10 Drawing Sheets

(51) Int. Cl.
*A61B 34/30* (2016.01)
*B25J 7/00* (2006.01)
*B25J 9/12* (2006.01)
*B25J 19/00* (2006.01)
*G05B 19/4155* (2006.01)
*H01F 7/02* (2006.01)
*H01F 7/06* (2006.01)
*H01F 27/24* (2006.01)
*H01F 27/28* (2006.01)

(52) U.S. Cl.
CPC ......... *H01F 27/24* (2013.01); *H01F 27/2823* (2013.01); *A61B 2034/731* (2016.02); *G05B 2219/40269* (2013.01); *G05B 2219/45073* (2013.01)

(56) References Cited

U.S. PATENT DOCUMENTS

2012/0281330 A1* 11/2012 Abbott .................. A61B 34/70
361/143
2022/0061642 A1* 3/2022 Park .................. A61B 1/00158

FOREIGN PATENT DOCUMENTS

| WO | WO-2020171443 A1 * | 8/2020 | ......... A61B 1/00158 |
| WO | WO-2020171446 A1 * | 8/2020 | ......... A61B 1/00036 |
| WO | WO-2021201362 A1 * | 10/2021 | ............ A61B 34/20 |

* cited by examiner

US 12,027,310 B2

DUAL HYBRID ELECTROMAGNET MODULE FOR CONTROLLING MICROROBOT

CROSS-REFERENCE TO RELATED APPLICATION

This application claims benefit of Korean Patent Application No. 10-2021-0013298, filed on Jan. 29, 2021. The entire disclosures of the applications identified in this paragraph are incorporated herein by reference.

FIELD

This research was supported by a grant of the Korea Health Technology R&D Project through the Korea Health Industry Development Institute (KHIDI), funded by the Ministry of Health & Welfare, Republic of Korea (grant number: HI19C0642).

The present disclosure relates to a dual hybrid electromagnet module for controlling a microrobot. More specifically, the present disclosure relates to an electromagnetic field system capable of being used for long-term surgery using a microrobot, in which a dual hybrid electromagnet module including a permanent magnet and an electromagnet is used for controlling a microrobot so that it is possible to reduce the number of used electromagnets so as to reduce power consumption and the amount of heat generated from the electromagnet module.

BACKGROUND

Electromagnetic field devices are being developed to drive microrobots in a human body from the outside of the human body. Wired or wireless microrobots are used depending on the purpose of a medical procedure in a human body, and technologies for driving microrobots by controlling the directions and intensities of magnetic fields using an electromagnetic field apparatus have been known or are being developed. Specifically, electromagnetic field devices, each having a fixed or movable system structure, in which a plurality of electromagnets/permanent magnets are arranged in consideration of a disease site in a human body and motion characteristics of a microrobot, are being developed.

A previously developed electromagnetic field driving device uses a large number of used electromagnets and thus a large device size, which makes it difficult to efficiently install and operate the device in a medical procedure space. In addition, the electromagnetic field device is inefficient in terms of various operations due to an increase in the number of power supplies for supplying power due to an increase in the number of electromagnets, which leads to, for example, an increase in power consumption.

In addition, a magnetic field driving device using a permanent magnet has a limitation in controlling a microrobot although the number of magnets used in the device is small. In addition, since the permanent magnets have a constant magnetization value, the robot is driven by the change of the distance between the robot and the magnets and the direction of the magnets, and has a limitation in control performance. Further, although a space for controlling the permanent magnets is secured using a motor, it is difficult to control magnetic fields in real time due to a time difference in the operation of the motor. In addition, in the case of a conventional method of controlling a robot by changing a gradient magnetic field and a uniform magnetic field in a space, there is a limitation in that it is difficult to locate the robot to a desired position without location information.

The inventors have completed dual hybrid electromagnet modules for controlling a microrobot and a microrobot control device using the same in order to solve the problems of the prior art described above.

SUMMARY

Accordingly, the inventors have found that with the electromagnetic field system according to the present disclosure, it is possible to significantly reduce the amount of heat generated by the electromagnet and power consumption while accurately controlling the position of a microrobot.

Therefore, in an aspect, the present disclosure is to provide an electromagnetic field system.

In another aspect, the present disclosure is to provide a method of driving a microrobot using the electromagnetic field system.

The present disclosure relates to a dual hybrid electromagnet module for controlling a microrobot. With the electromagnetic field system according to the present disclosure, it is possible to precisely drive a microrobot with small heat generation and power consumption.

Hereinafter, the present disclosure will be described in more detail.

An aspect of the present disclosure relates to an electromagnetic field system. The electromagnetic field system includes a first hybrid electromagnet module and a second hybrid electromagnet module. The first hybrid electromagnet module includes a first magnetic body including a first permanent magnet, and a first electromagnet including a first magnetic core and a first wire wound around the first magnetic core, the second hybrid electromagnet module includes a second magnetic body including a second permanent magnet, and a second electromagnet including a second magnetic core and a second wire wound around the second magnetic core, and the first hybrid electromagnet module and the second hybrid electromagnet module are arranged such that the central axis of the first hybrid electromagnet module and the central axis of the second hybrid electromagnet module cross each other so as to form an intersection point.

In an embodiment of the present disclosure, the first electromagnet or the second electromagnet may be one or more types of coils selected from a solenoid coil, a circular coil, a square coil, a Maxwell coil, a Helmholtz coil, and a saddle coil.

The term "circular coil" used herein may be interpreted as a circular electromagnet, and a circular electromagnet refers to a ring-shaped magnet, that is, an endless magnet that does not exhibit the effect of a demagnetization force at an end thereof.

In an embodiment of the present disclosure, the electromagnetic field system may further include a frame unit that interconnects the first hybrid electromagnet module and the second hybrid electromagnet module.

In an embodiment of the present disclosure, at least one of the first permanent magnet and the second permanent magnet may include a hollow central portion.

In an embodiment of the present disclosure, the first electromagnet and the first magnetic body may be arranged such that the first electromagnet is located farther from the intersection point, at which the central axes of the first hybrid electromagnet module and the second hybrid electromagnet module intersect, than the first magnetic body in the first hybrid electromagnet module, and the second electromagnet and the second magnetic body may be arranged such that the second electromagnet is located farther from the intersection point, at which the central axes of the first hybrid electromagnet module and the second hybrid electromagnet module intersect, than the second magnetic body in the second hybrid electromagnet module.

As used herein, the term "intersection point" refers to a virtual point at which a virtual axis penetrating the center of the first hybrid electromagnet module and a virtual axis penetrating the center of the second hybrid electromagnet module meet, but is not limited thereto. The intersection point may be located within a region of interest, which is an area in which a microrobot is to be driven.

Specifically, in the first hybrid electromagnet module or the second hybrid electromagnet module according to the present disclosure, the first electromagnet, the first magnetic body or the second electromagnet, and the second magnetic body may be arranged in that order from the intersection point.

When an electromagnet is located closer to the intersection point, the electromagnet, which is a main microrobot control device, is located at the bottom, which makes it possible to improve the performance of controlling the operation of a microrobot and to precisely operate the microrobot with a small current change.

In an embodiment of the present disclosure, the first hybrid electromagnet module and the second hybrid electromagnet module may be arranged such that the central axes of the first hybrid electromagnet module and the second hybrid electromagnet module form therebetween an angle corresponding to at least one of angle ranges of 1 to 90 degrees, 10 to 80 degrees, 10 to 70 degrees, 10 to 60 degrees, 10 to 50 degrees, 20 to 80 degrees, 20 to 70 degrees, 20 to 60 degrees, 20 to 50 degrees, and 20 to 40 degrees. For example, the first hybrid electromagnet module and the second hybrid electromagnet module may be arranged such that the central axes of the first hybrid electromagnet module and the second hybrid electromagnet module form an angle of 30 degrees therebetween, but are not limited thereto.

In an embodiment of the present disclosure, the magnetization directions of the first magnetic body and the first electromagnet may be parallel to the central axis of the first hybrid electromagnet module, and the magnetization directions of the second magnetic body and the second electromagnet may be parallel to the central axis of the second hybrid electromagnet module. Accordingly, the user may control the direction and amount of the current applied to each hybrid electromagnet module so as to control each hybrid electromagnet module to have a magnetic field direction toward the intersection point, or to set the magnetic field direction in the opposite direction to the intersection point.

In an embodiment of the present disclosure, the first magnetic body and the second magnetic body may be arranged such that the magnetic field directions of the first magnetic body and the second magnetic body are opposite to each other with respect to the intersection point.

In an embodiment of the present disclosure, the first hybrid electromagnet module and the second hybrid electromagnet module may be arranged such that the center axis of the first hybrid electromagnet module and the center axis of the second hybrid electromagnet module form an angle of 30 degrees therebetween, and the directions of magnetic fields of the first and second magnetic bodies are opposite to each other with respect to the intersection point. When the first hybrid electromagnet module and the second hybrid electromagnet module are arranged as described above, it is possible for the user to freely control the directions of magnetic fields in a range from −90 degrees to 60 degrees in a region of interest (ROI) by not applying a current to the electromagnet in each of the hybrid electromagnet modules or by adjusting the direction and intensity of the current applied to the electromagnet in each of the hybrid electromagnet modules (see FIG. 4 and FIGS. 5A to 5D).

In an embodiment of the present disclosure, at least one of the first electromagnet and the second electromagnet may include a solenoid coil.

In an embodiment of the present disclosure, the electromagnetic field system may further include a controller configured to control the first hybrid electromagnet module and the second hybrid electromagnet module.

In an embodiment of the present disclosure, the electromagnetic field system may further include a power supply configured to apply a current to the first hybrid electromagnet module and the second hybrid electromagnet module.

In an embodiment of the present disclosure, the electromagnetic field system may further include a cooling unit.

In an embodiment of the present disclosure, the frame unit may further include a shielding material.

In an embodiment of the present disclosure, the electromagnetic field system may further include an arm unit configured to move the first hybrid electromagnet module and the second hybrid electromagnet module.

In an embodiment of the present disclosure, the electromagnetic field system may further include a bed.

In an embodiment of the present disclosure, the first permanent magnet and the second permanent magnet may be rectangular or cylindrical.

Another aspect of the present disclosure relates to a method of driving a microrobot.

The method includes a driving operation of moving the microrobot into a region of interest (ROI) by applying a current to an electromagnetic field system wherein the electromagnetic field system includes a first hybrid electromagnet module and a second hybrid electromagnet module, the first hybrid electromagnet module including a first magnetic body including a first permanent magnet, and a first electromagnet including a first magnetic core and a first wire wound around the first magnetic core, the second hybrid electromagnet module including a second magnetic body including a second permanent magnet, and a second electromagnet including a second magnetic core and a second wire wound around the second magnetic core, and the first hybrid electromagnet module and the second hybrid electromagnet module are arranged such that the central axis of the first hybrid electromagnet module and the central axis of the second hybrid electromagnet module cross each other so as to form an intersection point.

As used herein, the term "microrobot" is a type of medical device that is inserted into a human body, and may be classified into a mechanical/electronic microrobot including a permanent magnet or a soft magnetic material having a millimeter scale size, such as a vascular robot or an active capsule endoscope, or a polymer/cell-based microrobot including magnetic nanoparticles as micro/nanometer scale size magnetic materials, such as a microcarrier for DDS, a cell therapeutic agent delivery microscaffold, a nanorobot, or a macrophage robot. Other types of microrobots may be included.

The microrobot according to the present disclosure may further include at least one selected from a group consisting of a camera module, a location information providing unit, a driving unit, a treatment unit, a robot controller, a data transmission/reception unit, and a wireless power reception unit.

In an embodiment of the present disclosure, the first electromagnet or the second electromagnet may be one or more types of coils selected from a solenoid coil, a circular coil, a square coil, a Maxwell coil, a Helmholtz coil, and a saddle coil.

In an embodiment of the present disclosure, the electromagnetic field system may further include a frame unit that interconnects the first hybrid electromagnet module and the second hybrid electromagnet module.

In an embodiment of the present disclosure, at least one of the first permanent magnet and the second permanent magnet may include a hollow central portion.

In an embodiment of the present disclosure, the first electromagnet and the first magnetic body may be arranged such that the first electromagnet is located farther from the intersection point, at which the central axes of the first hybrid electromagnet module and the second hybrid electromagnet module intersect, than the first magnetic body in the first hybrid electromagnet module, and the second electromagnet and the second magnetic body may be arranged such that the second electromagnet is located farther from the intersection point, at which the central axes of the first hybrid electromagnet module and the second hybrid electromagnet module intersect, than the second magnetic body in the second hybrid electromagnet module.

In an embodiment of the present disclosure, the first hybrid electromagnet module and the second hybrid electromagnet module may be arranged such that the central axes of the first hybrid electromagnet module and the second hybrid electromagnet module form therebetween an angle corresponding to at least one of angle ranges of 1 to 90 degrees, 10 to 80 degrees, 10 to 70 degrees, 10 to 60 degrees, 10 to 50 degrees, 20 to 80 degrees, 20 to 70 degrees, 20 to 60 degrees, 20 to 50 degrees, and 20 to 40 degrees. For example, the first hybrid electromagnet module and the second hybrid electromagnet module may be arranged such that the central axes of the first hybrid electromagnet module and the second hybrid electromagnet module form an angle of 30 degrees therebetween, but are not limited thereto.

In an embodiment of the present disclosure, the first magnetic body and the second magnetic body may be arranged such that the magnetic field directions of the first magnetic body and the second magnetic body are opposite to each other with respect to the intersection point.

In an embodiment of the present disclosure, the electromagnetic field system may further include a controller configured to control the first hybrid electromagnet module and the second hybrid electromagnet module.

In an embodiment of the present disclosure, the electromagnetic field system may further include a power supply configured to apply a current to the first hybrid electromagnet module and the second hybrid electromagnet module.

In an embodiment of the present disclosure, the electromagnetic field system may further include a cooling unit.

In an embodiment of the present disclosure, the frame unit may further include a shielding material.

In an embodiment of the present disclosure, the electromagnetic field system may further include an arm unit configured to move the first hybrid electromagnet module and the second hybrid electromagnet module.

In an embodiment of the present disclosure, the electromagnetic field system may further include a bed.

In an embodiment of the present disclosure, the first permanent magnet and the second permanent magnet may be rectangular or cylindrical.

The present disclosure relates to a dual hybrid electromagnet module for controlling a microrobot. More specifically, the present disclosure relates to an electromagnetic field system in which a dual hybrid electromagnet module including a permanent magnet and an electromagnet is used for controlling a microrobot so that it is possible to reduce the number of used electromagnets so as to reduce power consumption and the amount of heat generated from the electromagnet module. The electromagnetic field system is capable of being used for various medical procedures and surgeries using a microrobot.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

Figure 1:
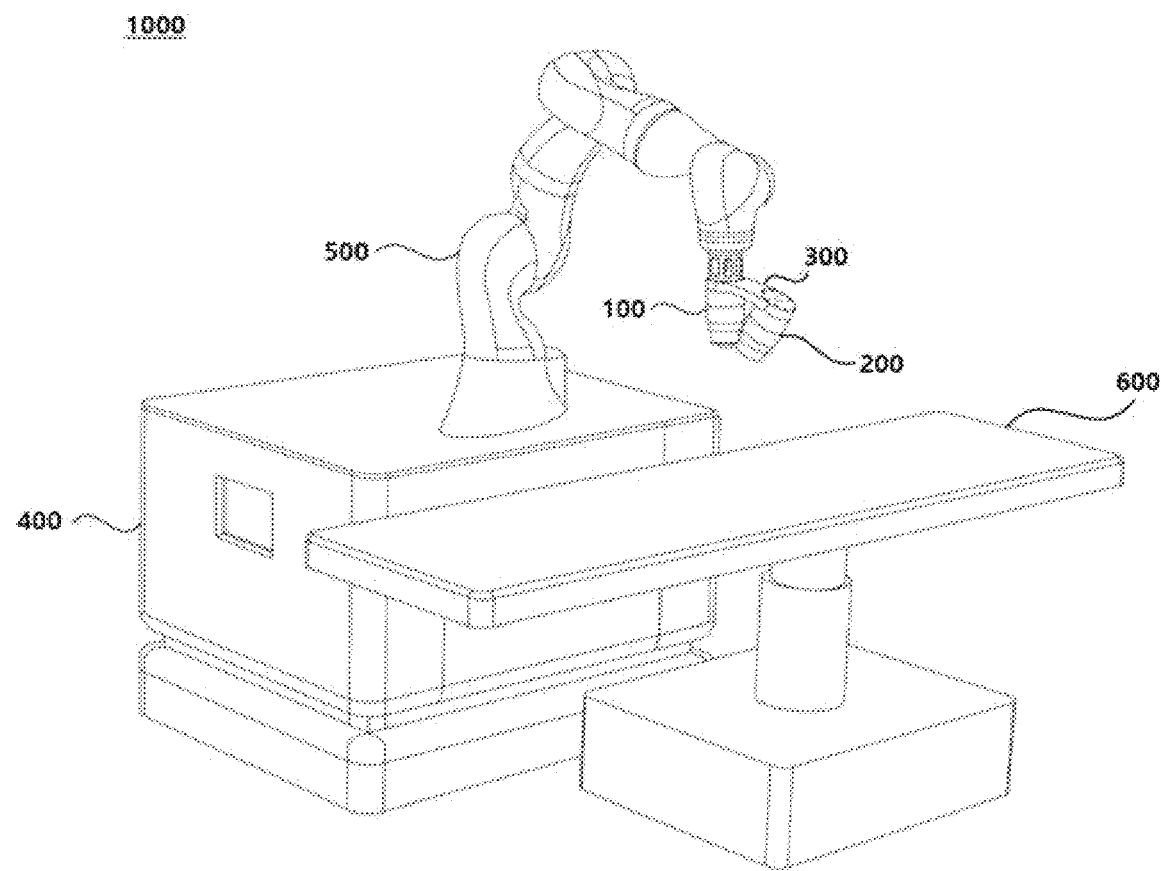
FIG. 1 is a view illustrating an electromagnetic field system according to an embodiment of the present disclosure.

Hereinafter, embodiments of the present disclosure will be described in detail with reference to the accompanying drawings. In the following description of the present disclosure, a detailed description of related known functions or configurations will be omitted when it is determined that the detailed description may make the subject matter of the present disclosure unnecessarily unclear.

Embodiments according to the concept of the present disclosure may be variously modified and may be implemented in various forms. Thus, specific embodiments are illustrated in the drawings, and will be described in detail in the present specification or application. However, it is to be understood that this is not intended to limit the embodiments according to the concept of the present disclosure to the specific disclosure forms, but includes all the modifications, equivalents, and substitutions that fall within the spirit and scope of the present disclosure.

When a constituent element is referred to as being "connected" or "coupled" to another constituent element, it should be understood that the constituent element may be directly connected or coupled to the other element, but a still another constituent element may be present therebetween.

Whereas, when a constituent element is referred to as being "directly connected" or "directly coupled" to another element, it should be understood that there is no constituent element therebetween. Other expressions that describe a relationship between constituent elements, such as "between" and "just between" or "neighboring to" and "directly neighboring to" should be interpreted in the same manner as the foregoing.

FIG. 1 is a view illustrating an electromagnetic field system 1000 according to an embodiment of the present disclosure.

Referring to FIG. 1, the electromagnetic field system 1000 according to an embodiment may include a first hybrid electromagnet module 100, a second hybrid electromagnet module 200, a frame 300, a main body 400, and an arm 500, and a bed 600.

The first hybrid electromagnet module 100 may be connected to the second hybrid electromagnet module 200 via the frame 300, and at least one of the first hybrid electromagnet module 100 and the second hybrid electromagnet module 200 connected via the frame 300 may be disposed so as to be connected to one end of the arm 500.

The first hybrid electromagnet module 100 and the second hybrid electromagnet module 200 may receive power from a power supply (not illustrated) included in the main body 400. The first hybrid electromagnet module 100 or the second hybrid electromagnet module 200 may receive power from the power supply via an electric wire disposed inside or outside the arm 500. In this case, the frame 300 may include an electric wire therein, and accordingly, the power supplied from the power supply may be supplied to the second hybrid electromagnet module 200 via the arm 500 and the frame 300.

In addition, the first hybrid electromagnet module 100 and the second hybrid electromagnet module 200 may be supplied with power from the power supply via wires that are directly connected to the hybrid electromagnet modules 100 and 200, respectively.

The first hybrid electromagnet module 100 and the second hybrid electromagnet module 200 may be disposed to face the bed 600, and thus, when an object is placed on the bed 600, the first hybrid electromagnet module 100 and the second hybrid electromagnet module 200 may be driven so as to control the microrobot within the region of interest located on the upper side of the bed 600.

The main body 400 may include a power supply (not illustrated).

The power supply may apply a current to the first hybrid electromagnet module 100 and the second hybrid electromagnet module 200 via an arm or directly from the inside of the main body 400. In addition, as will be described later, because the electromagnetic field system 1000 according to an embodiment uses the dual hybrid electromagnet modules 100 and 200, the power consumption is lower than that of the existing electromagnetic field system including only an electromagnet. Thus, it is possible for the power supply to supply a small amount of current to each of the hybrid electromagnet modules 100 and 200 so that the microrobot can be efficiently controlled.

The main body 400 may include a cooling unit (not illustrated), and the cooling unit may cool the first hybrid electromagnet module 100 and the second hybrid electromagnet module 200.

The arm 500 may be disposed on the top of the main body 400. The arm 500 may move the positions of the first hybrid electromagnet module 100 and the second hybrid electromagnet module 200. Accordingly, it is possible for the user to move each of the hybrid electromagnet modules 100 and 200 to apply a magnetic field to the region of interest.

Figure 2:
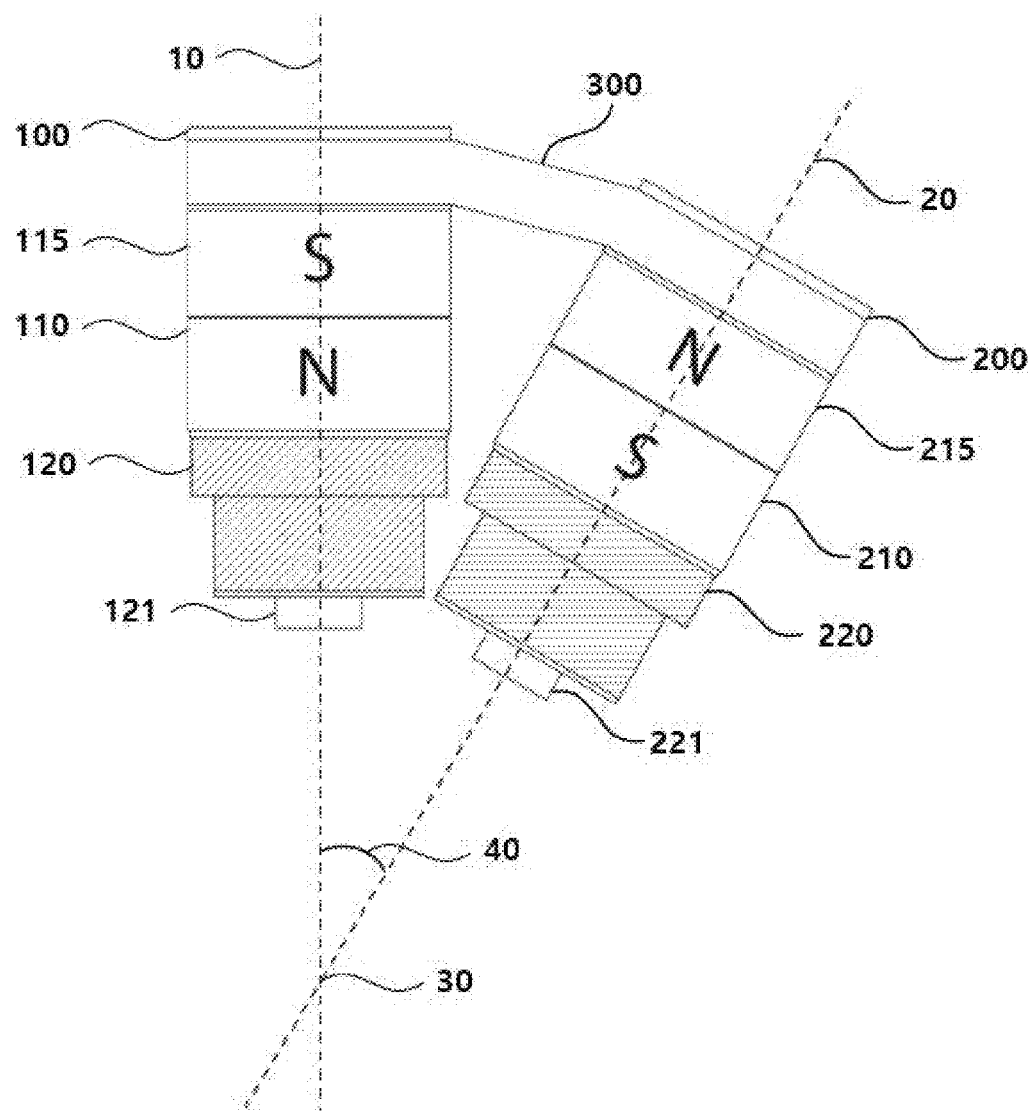
FIG. 2 is a view illustrating a dual hybrid electromagnet module according to an embodiment of the present disclosure.
Figure 3:
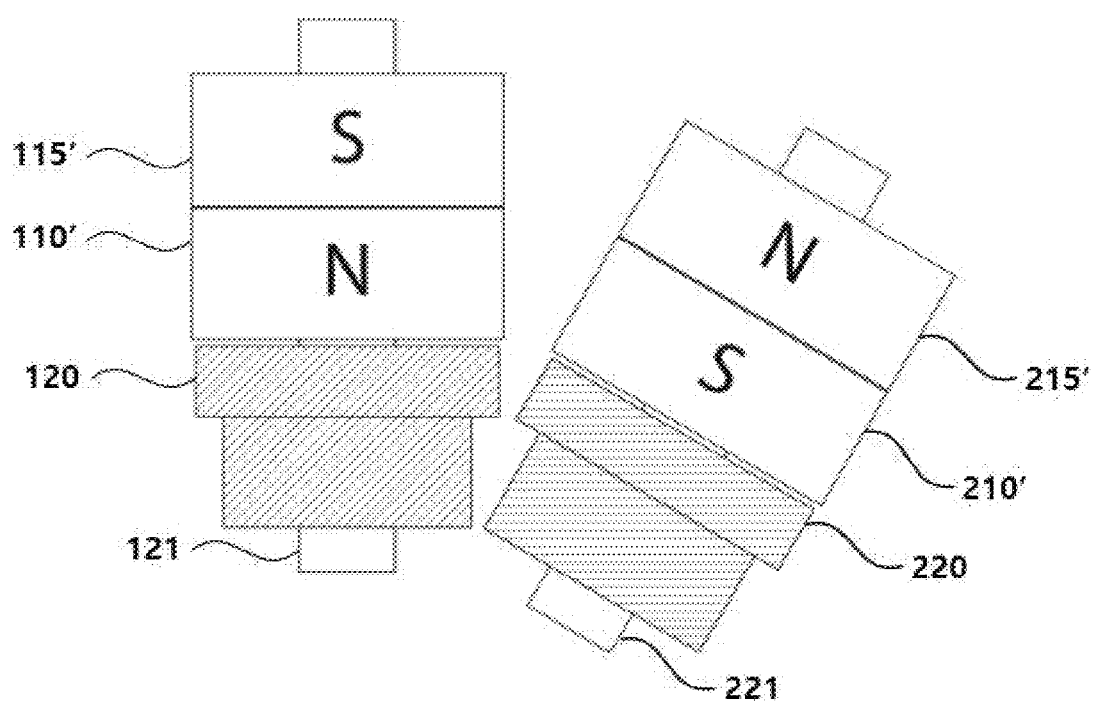
FIG. 3 is a view illustrating a dual hybrid electromagnet module according to another embodiment of the present disclosure.

FIG. 2 is a view illustrating a dual hybrid electromagnet module according to an embodiment of the present disclosure, and FIG. 3 is a view illustrating a dual hybrid electromagnet module according to another embodiment of the present disclosure.

Referring to FIGS. 2 to 3, the first hybrid electromagnet module 100 may include a first magnetic body 110 and a first electromagnet 120, and the second hybrid electromagnet module 200 may include a second magnetic body 210 and a second electromagnet 220.

Meanwhile, the first hybrid electromagnet module 100 and the second hybrid electromagnet module 200 may be arranged such that the central axis 10 of the first hybrid electromagnet module and the central axis 20 of the second hybrid electromagnet module intersect to each other so as to form an intersection point 30. When the central axis of each of the hybrid electromagnet modules is arranged so as to form the intersection point 30, the magnetic fields generated from each hybrid electromagnet module may be focused on the intersection point.

The central axis 10 of the first hybrid electromagnet module and the central axis 20 of the second hybrid electromagnet module may be arranged to form a predetermined angle 30 therebetween. The angle formed by the two central axes 10 and 20 is an angle corresponding to one of angle ranges of 1 to 90 degrees, 10 to 80 degrees, 10 to 70 degrees, 10 to 60 degrees, 10 to 50 degrees, 20 to 80 degrees, 20 to 70 degrees, 20 to 60 degrees, 20 to 50, and 20 to 40 degrees. For example, the angle may be 30 degrees, but is not limited thereto.

The first magnetic body 110 may include a first permanent magnet 115, and the second magnetic body 210 may include a second permanent magnet 215.

The first permanent magnet or the second permanent magnet may be one or more of a neodymium magnet, a ferrite magnet, an alnico magnet, a samarium cobalt magnet, and a rubber magnet, or a combination thereof, and may be, for example, a neodymium magnet, but is not limited thereto.

At this time, the first magnetic body 110 may be arranged such that the magnetization direction of the first hybrid electromagnet module 100 is parallel to the central axis 10 of the first hybrid electromagnet module, and the second magnetic body 210 may be arranged such that the magnetization direction of the second hybrid electromagnet module 200 is parallel to the central axis 20 of the second hybrid electromagnet module.

The first magnetic body 110 and the second magnetic body 210 may be arranged such that the magnetic field directions thereof are opposite to each other with respect to the intersection point 30. For example, as illustrated in FIGS. 2 to 3, in the first hybrid electromagnet module 110, the S pole of the first permanent magnet 115 may be disposed adjacent to the frame 300, and the N pole may be disposed adjacent to the first electromagnet 120. In the second hybrid electromagnet module 200, the S pole of the second permanent magnet 215 may be disposed adjacent to the second electromagnet 220, and the N pole may be disposed adjacent to the frame 300.

In addition, when the magnetic field directions of the first magnetic body 110 and the second magnetic body 210 are arranged to be opposite to each other with respect to the intersection point 30, it is possible to set the direction of magnetic fields in the region of interest (ROI) using only the permanent magnets even if no current is applied to the first electromagnet 120 and the second electromagnet 220.

At least one of the first permanent magnet 110 and the second permanent magnet 210 may include a hollow central portion. For example, as illustrated in FIG. 3, a first permanent magnet 110' and a second permanent magnet 210' may both include a hollow central portion.

The first electromagnet 120 may include a first magnetic core 121 and a first wire wound on the first magnetic core.

The second electromagnet 220 may include a second magnetic core 221 and a second wire wound on the second magnetic core.

The first electromagnet 120 and the second electromagnet 220 may be one or more types of coils selected from a solenoid coil, a circular coil, a square coil, a Maxwell coil, a Helmholtz coil, and a saddle coil, and may be, for example, a solenoid coil.

The first wire or the second wire may be an enameled wire, a copper wire, an enameled copper wire, or an enameled aluminum wire.

The frame 300 may connect the first hybrid electromagnet module 100 and the second hybrid electromagnet module 200 to each other.

The frame 300 may include a shielding material. When the shielding material is included in the frame 300, it is possible to suppress interference of magnetic fields generated from each of the first hybrid electromagnet module 100 and the second hybrid electromagnet module 200.

In the first hybrid electromagnet module 100 and the second hybrid electromagnet module 200, the first electromagnet 120 may be disposed to be located farther from the intersection point 30 than the first magnetic body 110 in the first hybrid electromagnet module 100, and the second electromagnet 220 may be disposed farther from the intersection point than the second magnetic body 210 in the second hybrid electromagnet module 200.

Figure 4:
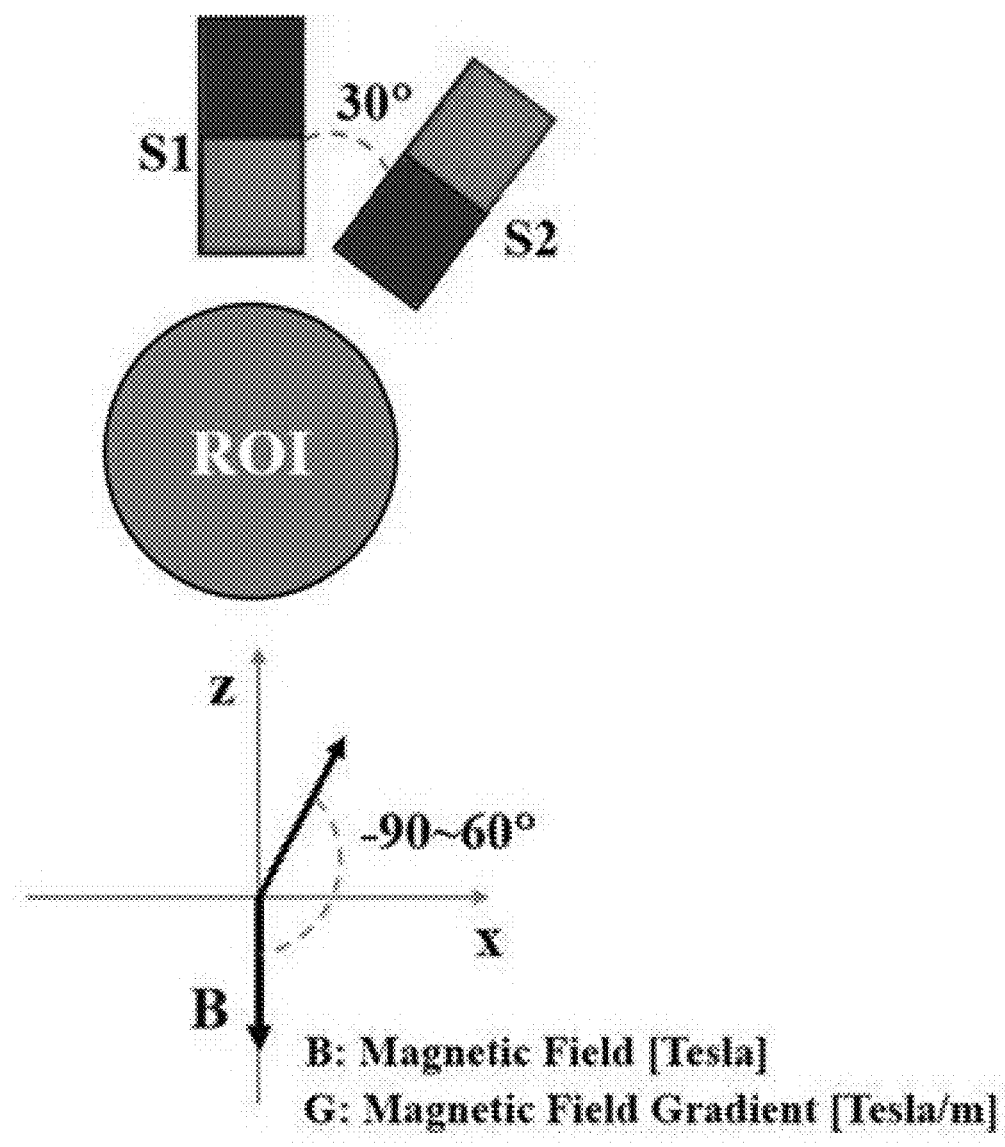
FIG. 4 is a view illustrating a magnetic field direction control range within a region of interest (ROI) of an electromagnetic field system according to an embodiment of the present disclosure.

FIG. 4 is a view illustrating a magnetic field direction control range within a region of interest (ROI) of an electromagnetic field system according to an embodiment of the present disclosure, and FIGS. 5A to 5D are views each illustrating a magnetic field direction according to an applied current value of each hybrid electromagnet module in an electromagnetic field system according to an embodiment of the present disclosure.

Referring to FIG. 4 and FIGS. 5A to 5D, when the first hybrid electromagnet module and the second hybrid electromagnet module are arranged to form an angle of 30 degrees therebetween, the electromagnetic field system according to the present disclosure may have a magnetic field direction control range between −90 degrees and 60 degrees in the region of interest.

Figure 5A:
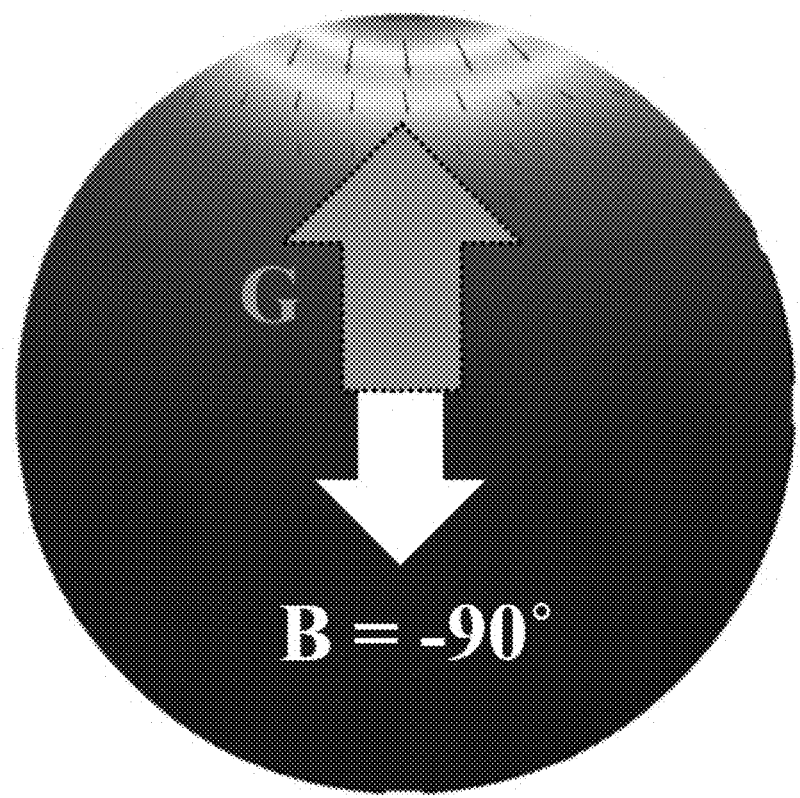
FIGS. 5A, 5B, 5C and 5D are views, each illustrating a magnetic field direction according to an applied current value of each hybrid electromagnet module in an electromagnetic field system according to an embodiment of the present disclosure.

Specifically, referring to FIG. 5A, when a current of −15 A is applied to the first hybrid electromagnet module S1 and a current of −10 A is applied to the second hybrid electromagnet module S2, the direction of the magnetic field may be controlled to −90 degrees. In this case, the first hybrid electromagnet module and the second hybrid electromagnet module may form magnetic fields regardless of the application of current. The magnetic fields of the first permanent magnet and the second permanent magnet may overlap, thereby forming magnetic fields in the 0 degree direction. In addition, a current is applied to each of the first and second electromagnets, and the magnetic fields may overlap the magnetic fields formed by the permanent magnets, thereby forming magnetic fields in the −90 degree direction.

Figure 5B:
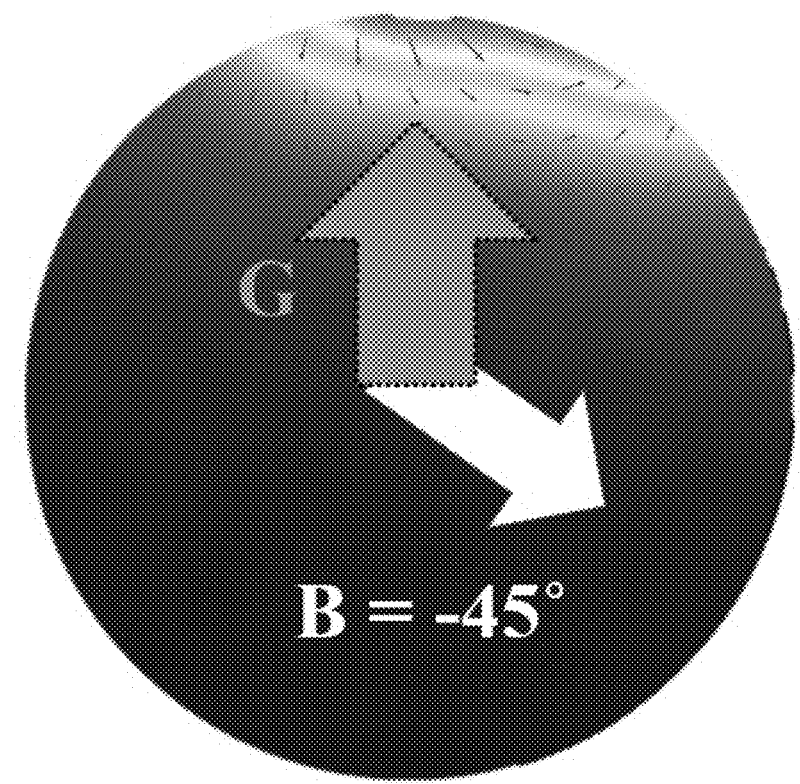

Furthermore, referring to FIG. 5B, when a current of −15 A is applied to the first hybrid electromagnet module and no current is applied to the second hybrid electromagnet module, the magnetic fields formed by the first electromagnet may overlap magnetic fields formed by the first permanent magnet and the second permanent magnet, thereby forming magnetic fields in the −45 degree direction.

Figure 5C:
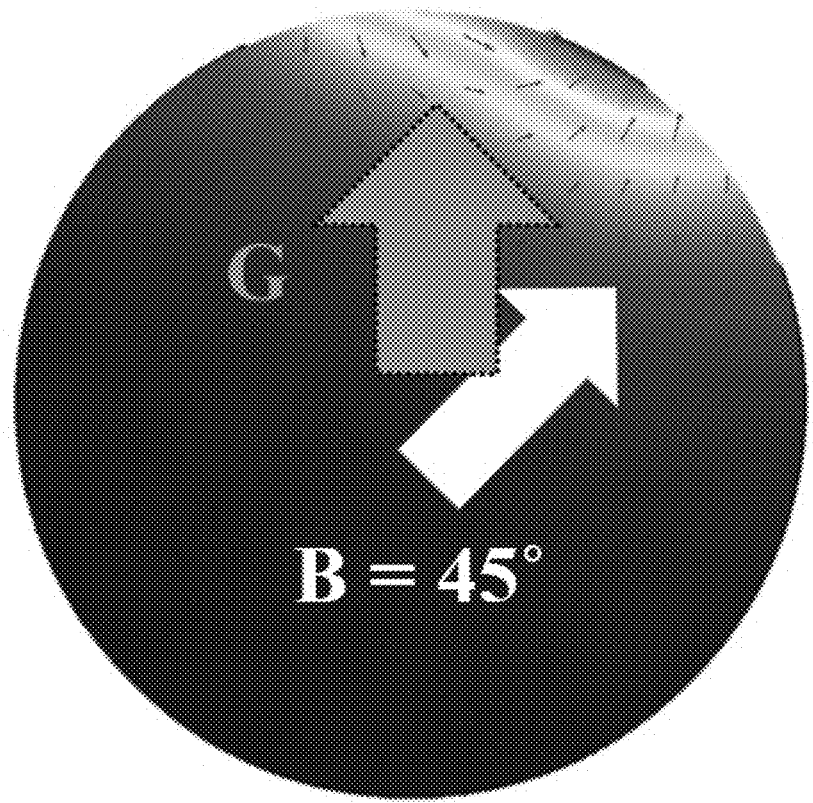
Figure 5D:
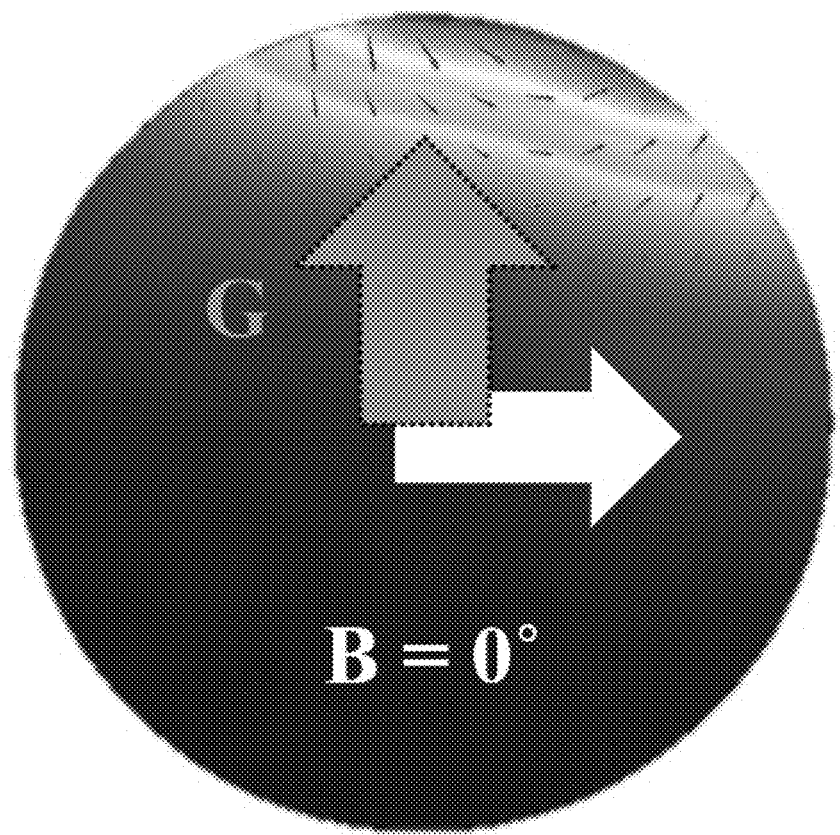

In addition, referring to FIG. 5c, when a current of −5 A is applied to the first hybrid electromagnet module and a current of 20 A is applied to the second hybrid electromagnet module, all the magnetic fields generated by the first electromagnet, the second electromagnet, the first permanent magnet and the second permanent magnet may overlap, thereby forming magnetic fields in the direction of 45 degrees.

Finally, as described above, when magnetic fields are formed only with the permanent magnets without applying a current to the first and second electromagnets, it is possible to form magnetic fields in the direction of 0 degrees depending on the angle (30 degrees) formed between the first and second permanent magnets.

As described above, in the electromagnetic field system according to an embodiment, each hybrid electromagnet module includes a permanent magnet as well as an electromagnet, and as the hybrid electromagnet modules are arranged to form a certain angle therebetween, it is possible to form magnetic fields in a predetermined direction without applying a current to the hybrid electromagnet modules. In addition, it is possible to freely form magnetic fields in a direction ranging from −90 degrees to 60 degrees in the region of interest by appropriately adjusting the direction and intensity of the current applied to each hybrid electromagnet module.

Accordingly, it is possible for the electromagnetic field system according to an exemplary embodiment to form magnetic fields in a predetermined direction even when no current is applied thereto. Thus, it is possible to implement a magnetic field system that neither consumes power nor generates heat. In addition, because the number of electromagnets used in the entire system is minimized, it is possible to reduce the power consumption of the power supply, and to drive the system without reducing the cooling capacity of the cooling unit or providing an additional cooling device. In addition, because the power consumption and heat generation of the entire system are minimized, it is possible to use the system for long-term medical procedures or surgeries using microrobots.

Embodiment 1: Confirmation of Driving of Microrobot by Electromagnetic Field System Two hybrid electromagnet modules each including a neodymium permanent magnet and an electromagnet were manufactured, connected to the frame, and attached to the robot arm, and then a test was conducted to drive a microrobot.

Each hybrid electromagnet module was controlled with or without a current applied to each of the hybrid electromagnet modules. A capsule-type robot manufactured as a prototype was placed in a transparent plastic cylindrical environment, and the position change of the robot was measured while changing the directions and intensities of the currents applied to the hybrid electromagnet modules.

Figure 6:
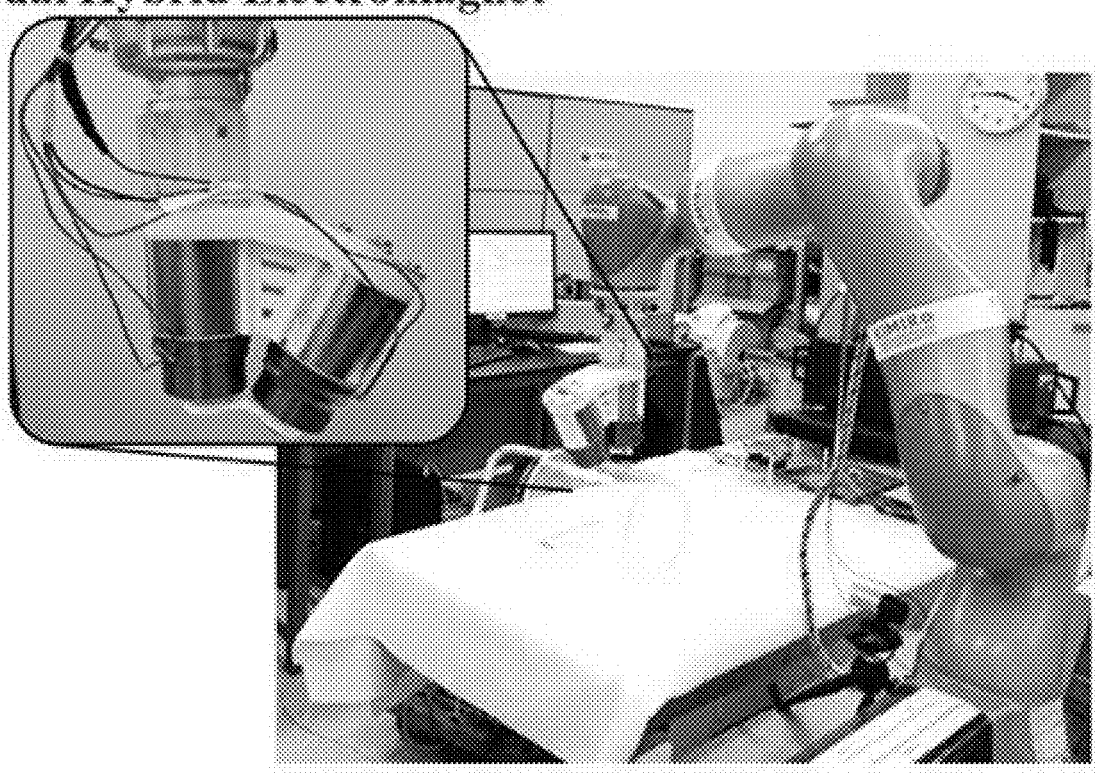
FIG. 6 is a photograph illustrating a prototype of an electromagnetic field system according to an embodiment of the present disclosure.
Figure 7:
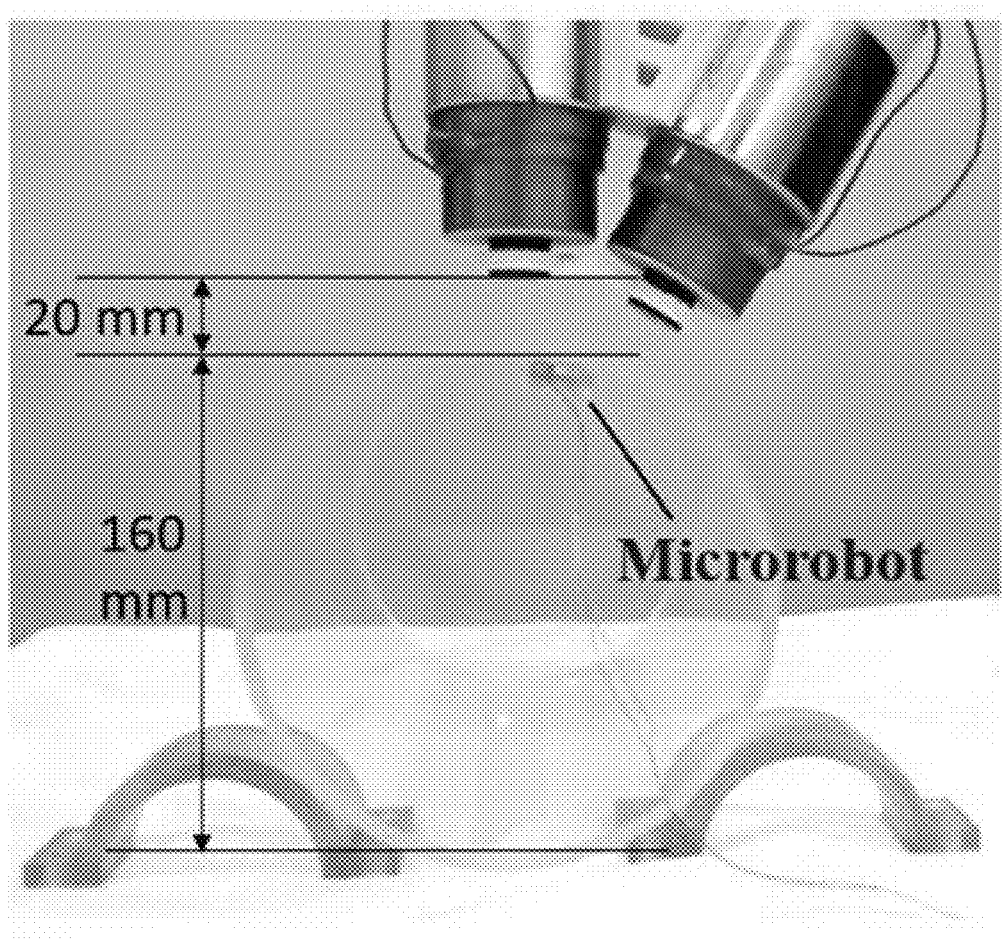
FIG. 7 is a photograph obtained by capturing a scene in which the prototype of the electromagnetic field system according to an embodiment of the present disclosure drives a microrobot.

As a result of the measurement, it was confirmed that five degrees of freedom of the capsule-type robot, that is, three degrees of freedom for position movement and two degrees of freedom for angular movement, were precisely controlled, as can be seen from FIGS. 6 to 7. In this case, it was confirmed that the power consumed by the entire electromagnetic field system was significantly reduced.

The present disclosure described above can be variously substituted, modified, and changed by a person ordinarily skill in the art to which the present disclosure belongs without departing from the technical spirit thereof. Therefore, the scope of protection of the present disclosure is not limited by the above-described embodiments and the accompanying drawings.

What is claimed is:

1. An electromagnetic field system comprising:
   a first hybrid electromagnet module; and
   a second hybrid electromagnet module,
   wherein the first hybrid electromagnet module comprises a first magnetic body comprising a first permanent magnet, and a first electromagnet comprising a first magnetic core and a first wire wound around the first magnetic core,
   the second hybrid electromagnet module comprises a second magnetic body comprising a second permanent magnet, and a second electromagnet comprising a second magnetic core and a second wire wound around the second magnetic core, and
   the first hybrid electromagnet module and the second hybrid electromagnet module are arranged such that a central axis of the first hybrid electromagnet module and a central axis of the second hybrid electromagnet module cross each other so as to form an intersection point,
   wherein the first electromagnet and the first magnetic body are arranged such that the first electromagnet is located farther from the intersection point, at which the central axes of the first hybrid electromagnet module and the second hybrid electromagnet module intersect, than the first magnetic body in the first hybrid electromagnet module, and
   the second electromagnet and the second magnetic body are arranged such that the second electromagnet is located farther from the intersection point, at which the central axes of the first hybrid electromagnet module and the second hybrid electromagnet module intersect, than the second magnetic body in the second hybrid electromagnet module.

2. The electromagnetic field system of claim 1, further comprising a frame unit that interconnects the first hybrid electromagnet module and the second hybrid electromagnet module.

3. The electromagnetic field system of claim 2, wherein the frame unit comprises a shielding material.

4. The electromagnetic field system of claim 1, wherein at least one of the first permanent magnet and the second permanent magnet comprises a hollow central portion.

5. The electromagnetic field system of claim 1, wherein the first hybrid electromagnet module and the second hybrid electromagnet module are arranged such that the central axis of the first hybrid electromagnet module and the central axis of the second hybrid electromagnet module form an angle ranging from 20 to 40 degrees therebetween.

6. The electromagnetic field system of claim 1, wherein magnetization directions of the first magnetic body and the first electromagnet are parallel to the central axis of the first hybrid electromagnet module, and
magnetization directions of the second magnetic body and the second electromagnet are parallel to the central axis of the second hybrid electromagnet module.

7. The electromagnetic field system of claim 1, wherein the first magnetic body and the second magnetic body are arranged such that magnetic field directions of the first magnetic body and the second magnetic body are opposite to each other with respect to the intersection point.

8. The electromagnetic field system of claim 1, wherein at least one of the first electromagnet and the second electromagnet comprises a solenoid coil.

9. The electromagnetic field system of claim 1, further comprising a controller configured to control the first hybrid electromagnet module and the second hybrid electromagnet module.

10. The electromagnetic field system of claim 1, further comprising a power supply configured to apply a current to the first hybrid electromagnet module and the second hybrid electromagnet module.

11. The electromagnetic field system of claim 1, further comprising a cooling unit.

12. The electromagnetic field system of claim 1, further comprising an arm unit configured to move the first hybrid electromagnet module and the second hybrid electromagnet module.

13. The electromagnetic field system of claim 1, further comprising a bed.

14. The electromagnetic field system of claim 1, wherein the first permanent magnet and the second permanent magnet are rectangular or cylindrical.

15. A method of driving a microrobot, the method comprising:
    a driving operation of moving the microrobot into a region of interest (ROI) by applying a current to an electromagnetic field system,
    wherein the electromagnetic field system comprises a first hybrid electromagnet module and a second hybrid electromagnet module,
    the first hybrid electromagnet module comprises a first magnetic body comprising a first permanent magnet, and a first electromagnet comprising a first magnetic core and a first wire wound around the first magnetic core, and
    the second hybrid electromagnet module comprises a second magnetic body comprising a second permanent magnet, and a second electromagnet comprising a second magnetic core and a second wire wound around the second magnetic core, and
    the first hybrid electromagnet module and the second hybrid electromagnet module are arranged such that a central axis of the first hybrid electromagnet module and a central axis of the second hybrid electromagnet module cross each other so as to form an intersection point,
    wherein, the first electromagnet and the first magnetic body are arranged such that the first electromagnet is located farther from the intersection point, at which the central axes of the first hybrid electromagnet module and the second hybrid electromagnet module intersect, than the first magnetic body in the first hybrid electromagnet module, and
    the second electromagnet and the second magnetic body are arranged such that the second electromagnet is located farther from the intersection point, at which the central axes of the first hybrid electromagnet module and the second hybrid electromagnet module intersect, than the second magnetic body in the second hybrid electromagnet module.

16. The method of claim 15, wherein the first magnetic body and the second magnetic body are arranged such that magnetic field directions of the first magnetic body and the second magnetic body are opposite to each other with respect to the intersection point.

* * * * *